(12) United States Patent
Kuo et al.

(10) Patent No.: US 9,603,811 B2
(45) Date of Patent: Mar. 28, 2017

(54) PHARMACEUTICAL COMPOSITIONS OF CAROTENOID CHYLOMICRONS

(71) Applicant: HEALTH-EVER BIOTECH CO. LTD, Taipei (TW)

(72) Inventors: Fu Feng Kuo, Taipei (TW); Bin-huei Chen, Taipei (TW)

(73) Assignee: Health-Ever Biotech Co., Ltd, Taipei (TW)

(*) Notice: Subject to any disclaimer, the term of this patent is extended or adjusted under 35 U.S.C. 154(b) by 0 days.

(21) Appl. No.: 14/770,704

(22) PCT Filed: Dec. 9, 2014

(86) PCT No.: PCT/IB2014/066737
§ 371 (c)(1),
(2) Date: Aug. 26, 2015

(87) PCT Pub. No.: WO2015/087242
PCT Pub. Date: Jun. 18, 2015

(65) Prior Publication Data
US 2016/0271076 A1    Sep. 22, 2016

Related U.S. Application Data

(60) Provisional application No. 61/914,879, filed on Dec. 11, 2013.

(51) Int. Cl.
| | | |
|---|---|---|
| A23K 50/00 | (2016.01) | |
| A61K 31/015 | (2006.01) | |
| A23L 33/00 | (2016.01) | |
| A23L 15/00 | (2016.01) | |
| A23K 50/10 | (2016.01) | |
| A23K 20/158 | (2016.01) | |
| A23J 7/00 | (2006.01) | |
| A23K 20/168 | (2016.01) | |
| A61K 47/14 | (2017.01) | |
| A61K 45/06 | (2006.01) | |
| A61K 31/01 | (2006.01) | |
| A61K 31/355 | (2006.01) | |
| A61K 31/575 | (2006.01) | |
| A61K 31/685 | (2006.01) | |
| A61K 31/7032 | (2006.01) | |
| A61K 9/00 | (2006.01) | |
| A61K 47/24 | (2006.01) | |
| A61K 47/44 | (2017.01) | |
| A61K 9/127 | (2006.01) | |
| A61K 9/107 | (2006.01) | |
| A61K 47/22 | (2006.01) | |
| A61K 9/51 | (2006.01) | |

(52) U.S. Cl.
CPC ........... *A61K 31/015* (2013.01); *A23J 7/00* (2013.01); *A23K 20/158* (2016.05); *A23K 20/168* (2016.05); *A23K 50/10* (2016.05); *A23L 15/30* (2016.08); *A23L 33/40* (2016.08); *A61K 9/0095* (2013.01); *A61K 9/107* (2013.01); *A61K 9/1075* (2013.01); *A61K 9/127* (2013.01); *A61K 9/5123* (2013.01); *A61K 31/01* (2013.01); *A61K 31/355* (2013.01); *A61K 31/575* (2013.01); *A61K 31/685* (2013.01); *A61K 31/7032* (2013.01); *A61K 45/06* (2013.01); *A61K 47/14* (2013.01); *A61K 47/22* (2013.01); *A61K 47/24* (2013.01); *A61K 47/44* (2013.01); *A23V 2002/00* (2013.01)

(58) Field of Classification Search
CPC ......... A23L 15/30; A23L 33/40; A23K 50/10; A23K 50/00; A23K 20/158; A23K 20/168; A23V 2002/00; A23J 7/00
See application file for complete search history.

(56) References Cited

U.S. PATENT DOCUMENTS

| | | | | |
|---|---|---|---|---|
| 4,474,773 | A * | 10/1984 | Shinitzky | ............... C11B 3/006 514/78 |
| 6,075,058 | A | 6/2000 | Handelman | |
| 2009/0312287 | A1 | 12/2009 | Kuo | |

FOREIGN PATENT DOCUMENTS

| | | |
|---|---|---|
| CA | 2556223 | 9/2005 |
| CA | 2825860 | 8/2012 |
| CA | 2857575 | 6/2013 |
| CA | 2858496 | 6/2013 |
| CN | 1561218 A | 1/2005 |
| EP | 2468111 A1 | 6/2012 |
| TW | I288614 B | 10/2007 |
| WO | 03009704 A2 | 2/2003 |
| WO | WO 03009704 * | 2/2003 |
| WO | 2013/021041 A1 | 2/2013 |

OTHER PUBLICATIONS

International Search Report issued in corresponding International Application No. PCT/IB2014/066737 on Apr. 29, 2015.
Author Unknown "The Research Status of the Health Care Function of Tomato Lycopene", (2007) China Natural Resources Network. Article at http://www.cntrxyz.com/article/showArticle.asp?ArticleID=590, 8 pages.
Author Unknown "Phytosterol" (2008), Plant Sterol at nutritionist Heath Corner at http://blog.xuite.net/jc721111241/twblog/136988023-%E6%A4%8D%E7%89%A9%E5%9B%BA%E9%86%87, 4 pages.

(Continued)

*Primary Examiner* — Carlos Azpuru
(74) *Attorney, Agent, or Firm* — Osha Liang LLP

(57) ABSTRACT

The present invention provides pharmaceutical compositions comprising a chylomicron and a carotenoid. The present invention also provides pharmaceutical compositions comprising a micelle and a carotenoid, suspended in an aqueous solution and suitable for intravenous administration. The bioavailability of the carotenoid of the pharmaceutical composition is higher relative to the bioavailability of free carotenoid.

18 Claims, No Drawings

(56) References Cited

OTHER PUBLICATIONS

Translation of Office Action issued in corresponding Korean Application No. 10-2016-7008688 dated Jul. 15, 2016 (6 pages).
Francis, F. Jack et al. "Natural Food Colorants" Science and Technology, Marcel Dekker, Inc., 2000, p. 161 (4 pages).
Office Action dated Sep. 27, 2016, issued by the U.S. Patent and Trademark Office in related U.S. Appl. No. 14/922,351 (6 pages).

* cited by examiner

PHARMACEUTICAL COMPOSITIONS OF CAROTENOID CHYLOMICRONS

CROSS REFERENCE TO RELATED APPLICATIONS

This application is a national stage under 35 U.S.C. 371 based on and claiming the benefit of International Application PCT/IB2014/066737, filed on Dec. 9, 2014, incorporated by reference, which claims the benefit of priority from U.S. Provisional Application No. 61/914,879, filed Dec. 11, 2013, the entire contents of each of which are incorporated herein by reference.

TECHNOLOGY FIELD

The present invention relates to pharmaceutical compositions comprising (a) one or more chylomicrons or one or more micelles; and (b) at least one carotenoid.

BACKGROUND OF THE INVENTION

Carotenoids are a class of hydrocarbon compounds that can be chemically subdivided into xanthophylls (oxygenated molecules) and carotenes (hydrocarbons lacking oxygen). Carotenes, such as solanorubin and its precursors hexahydrogenosolanorubin and octohydrogenosolanorubin, are commonly found in tomatoes, and may lower the risk of cardiovascular disease. Solanorubin extracted from tomato is a dark-red viscous liquid and insoluble in water.

The clinical use of solanorubin is limited by its instability and low bioavailability. Solanorubin is susceptible to isomerization or degradation when exposed to heat, light, oxygen, acid or metal ion. Previous study has shown the bioavailability of solanorubin from natural sources is at about 1.85%. (Faisal et al "Bioavailability of solanorubin in the rat: the role of lymphatic transport. J. Pharm. Pharmacol. 2010, March 62(3):323-31).

In view of the health benefits conferred by carotenoids and the low bioavailability and instability outlined above, there is a need for providing a composition comprising carotenoids with improved bioavailability and stability.

BRIEF SUMMARY OF THE INVENTION

In one embodiment, the present invention is directed to pharmaceutical compositions comprise (a) a chylomicron comprising a mixture of triglyceride, phospholipid and phytosterol, wherein the ratio of triglyceride:phospholipid:phytosterol relative to the pharmaceutical composition ranges from about 80:5:0.1 (w/w) to about 92:12:1 (w/w); and (b) a carotenoid.

In another embodiment, the pharmaceutical compositions of the present invention comprise (a) a micelle comprising a mixture of surfactant and phospholipid, wherein the ratio of surfactant:phospholipid ranges from about 5:0.01 (w/w) to about 20:0.5 (w/w) relative to the pharmaceutical composition; and (b) a carotenoid.

The terms "invention," "the invention," "this invention" and "the present invention" used in this patent or patent application are intended to refer broadly to all of the subject matter of this patent and the patent claims below. Statements containing these terms should be understood not to limit the subject matter described herein or to limit the meaning or scope of the patent claims below.

The invention will become more apparent when read with the detailed description which follows.

DETAILED DESCRIPTION OF THE INVENTION

Definition

As employed above and throughout the disclosure, the following terms, unless otherwise indicated, shall be understood to have the following meanings.

As used herein, the singular forms "a," "an," and "the" include the plural reference unless the context clearly indicates otherwise.

The term "subject" can refer to a vertebrate having prostate disease or to a vertebrate deemed to be in need of prostate disease treatment. Subjects include warm-blooded animals, such as mammals, such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, mouse, rabbit, rat, gerbil, guinea pig, etc.). Thus, veterinary uses and medical formulations are contemplated herein.

All numbers herein are understood as maybe modified by "about."

Pharmaceutical Composition

In one embodiment, the pharmaceutical compositions of the present invention comprise (a) one or more chylomicrones; and (b) one or more carotenoids, wherein the bioavailability of the carotenoid encapsulated in the chylomicron is higher relative to the bioavailability of said carotenoid not encapsulated in the chylomicron. In one embodiment, the encapsulation efficiency of the pharmaceutical composition is higher than 50, 60, 70, 80%.

In one exemplary embodiment, the chylomicron comprises a mixture of triglyceride, phospholipid and phytosterol, wherein the ratio of triglyceride:phospholipid:phytosterol relative to the pharmaceutical composition ranges from about 75:1:0.1 (w/w) to about 95:15:1.5 (w/w). In another exemplary embodiment, the ratio of triglyceride:phospholipid:phytosterol relative to the pharmaceutical composition ranges from about 80:6:0.1 (w/w) to about 92:12:1 (w/w). Without being bound by any particular theory, it is believed that the weight percent of the triglyceride:phospholipid:phytosterol plays an important role in the formation of the carotenoid chylomicron. This is because the highly viscous carotenoids (such as solanorubin) cannot or difficult to form chylomicrons. The formation of chylomicrons improves the bioavailability and stability of the encapsulated carotenoid.

In one exemplary embodiment, about 75 to about 95 weight % of the composition is a triglyceride. In an exemplary embodiment, the weight % of the triglyceride of the composition is equal to or less than about 94, 93, 92, 91, 90, 89, 88, 87, 86, 85, 84, 83, 82, 81, 80, 79, 78, 77, 76 or 75 or any value or range of values therebetween in 0.1% increments (e.g., about 86.5%, about 83.2%, etc.). In another exemplary embodiment, the weight % of the triglyceride of the composition is equal to or less than about 50, 49, 48, 47, 46, 45, 44, 43, 42, 41, 40, 39, 38, 37, 36, 35, 34, 33, 32, 31 or 30 or any value or range of values therebetween in 0.1% increments (e.g., about 48.7%, about 33.9%, about 33-48% etc.).

In one exemplary embodiment, about 1 to about 15 weight percent of the composition is a phospholipid. In another exemplary embodiment, about 6 to about 12 weight percent of the composition is a phospholipid. In yet another exemplary embodiment, the weight % of the phospholipid of the composition is equal to or less than about 14, 13, 12, 11, 10, 9, 8, 7, 6, 5, 4, 3, 2, 1 or any value or range of values therebetween in 0.1% increments (e.g., about 7.1%, about 8.3%, about 8-10% etc.). In another exemplary embodiment, the weight % of the phospholipid of the composition is equal to or less than about 5, 4, 3, 2 or any value or range of values therebetween in 0.1% increments (e.g., about 4.5%, about 2.1%, about 0.1-5% etc.).

In one embodiment, about 1 to about 3 weight percent of the composition is a phytosterol. In an exemplary embodiment, the weight % of phytosterol of the composition is equal to or less than about 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1 or any value or range of values therebetween in 0.01% increments (e.g., about 1.71%). In another exemplary embodiment, the weight % of the phospholipid relative to the composition is about 0.1 to about 1.5. In yet another exemplary embodiment, the weight % of phytosterol relative to the composition is equal to or less than about 1.4, 1.3, 1.2, 1.1, 1.0, 0.9, 0.8, 0.7, 0.6, 0.5, 0.4, 0.3, 0.2, 0.1 or any value or range of values therebetween in 0.01% increments (e.g., about 0.71%).

In one embodiment, the pharmaceutical composition further comprises about 0.01 weight % to about 1 weight % beta-carotene. In another embodiment, the weight % of beta-carotene relative to the composition is equal to or less than about 0.9, 0.8, 0.7, 0.6, 0.5, 0.4, 0.3, 0.2, 0.1 or any value or range of values therebetween in 0.01% increments (e.g., about 0.14%).

The diameter of the chylomicron in the pharmaceutical composition maybe greater than or equal to about 75 nm, such as, for example, about 80 nm, about 85 nm, about 90 nm, about 95 nm, about 100 nm, about 105 nm, about 110 nm, about 115 nm, about 120 nm, and about 125 nm, about 130 nm, about 135 nm, and about 140 nm. The diameter of the chylomicron in the pharmaceutical composition maybe less or equal to about 450 nm, such as, for example, about 445 nm, about 440 nm, and about 435 nm. In one embodiment, the diameter of the chylomicron in the pharmaceutical composition is about 100 to about 150 nm. In another embodiment, the diameter of the chylomicron in the pharmaceutical composition is about 125 nm to about 140 nm. In yet another embodiment, the diameter of the chylomicron in the pharmaceutical composition is about 130 nm to about 135 nm. In yet another embodiment, the diameter of the chylomicron in the pharmaceutical composition is about 125 nm to about 140 nm In one embodiment, the carotenoids which are suitable for use in the present invention are carotenes. Non limiting examples of carotenes include alpha-carotene, beta-carotene, solanorubin and its precursors hexahydrogenosolanorubin and octohydrogenosolanorubin. In another embodiment, the carotenoids which are suitable for us in the present invention are xanthophylls. Non limiting examples of xanthophylls include beta-cryptoxanthin, lutein, and zeaxanthin.

In one embodiment, the carotenoid is selected from one or more of the following: solanorubin; octohydrogenosolanorubin or hexahydrogenosolanorubin. In another embodiment, the carotenoid is substantially free of xanthophyll. In another embodiment, xanthophyll is preferably present in the composition in an amount of ≤2 weight %, more preferably ≤1.5 weight %, even more preferably ≤1 weight %, and most preferably ≤0.5 weight %.

In one embodiment, the pharmaceutical composition is substantially free of zein protein. In another embodiment, zein protein is preferably present in the composition in an amount of ≤2 weight %, more preferably ≤1.5 weight %, even more preferably ≤1 weight %, and most preferably ≤0.5 weight %.

In one embodiment, the pharmaceutical composition is substantially free of amino acid. In another embodiment, zein protein is preferably present in the composition in an amount of ≤2 weight %, more preferably ≤1.5 weight %, even more preferably ≤1 weight %, and most preferably ≤0.5 weight %.

The pharmaceutical composition may be constituted into any form suitable for the mode of administration selected. Preferably, the pharmaceutical composition is formulated for oral administration. Other medically acceptable route of administration includes intravenous, subcutaneous, intramuscular, transdermal, rectal or inhalation and the like. In one embodiment, the pharmaceutical composition is optionally constituted with about 1-10 mL of deionized water containing 0.1 g-1.5 g of phospholipid (e.g., lecithin). In another embodiment, the volume of water for constitution is equal to or less than about 9, 8, 7, 6, 5, 4, 3, 2 ml, or any value or range of values therebetween in 0.1% increments (e.g., about 4-6 ml, about 5.4 ml). In yet another embodiment, the weight of the phospholipid for constitution is equal to or less than about 1.4, 1.3, 1.2, 1.1, 1.0, 0.9, 0.8, 0.7, 0.6, 0.5, 0.4, 0.3, 0.2 g, or any value or range of values therebetween in 0.01% increments (e.g., about 0.45-0.75 g, about 6 g).

The dosage of the pharmaceutical composition or the carotenoid can be determined by the skilled person in the art according to the embodiments. Unit doses or multiple dose forms are contemplated, each offering advantages in certain clinical settings. According to the present invention, the actual amount of carotenoid or pharmaceutical composition to be administered can vary in accordance with the age, weight, condition of the subject to be treated and other co-morbidity, and depends on the discretion of medical professionals. In one embodiment, about 1 to about 10 weight percent of the composition is solanorubin, about 0.1 to about 1.5 weight percent of the composition is octohydrogenosolanorubin, and about 0.1 to about 1.5 weight percent of the composition is hexahydrogenosolanorubin. In another embodiment, about 2 to about 6 weight % of the composition is solanorubin, about 0.2 to about 0.6 weight % of the composition is octohydrogenosolanorubin, and about 0.1 to about 0.5 weight % of the composition is hexahydrogenosolanorubin. In an exemplary embodiment, the weight % of solanorubin relative to the chylomicron composition is equal to or less than about 9, 8, 7, 6, 5, 4, 3, 2, or any value or range of values therebetween in 0.1% increments (e.g., about 4.3%). In another exemplary embodiment, the weight % of octohydrogenosolanorubin relative to the chylomicron composition is equal to or less than about 1.4, 1.3, 1.2, 1.1, 1.0, 0.9, 0.8, 0.7, 0.6, 0.5, 0.4, 0.3, 0.2 or any value or range of values therebetween in 0.01% increments (e.g., about 0.43%). In yet another exemplary embodiment, the weight % of hexahydrogenosolanorubin relative to the chylomicron composition is equal to or less than about 1.4, 1.3, 1.2, 1.1, 1.0, 0.9, 0.8, 0.7, 0.6, 0.5, 0.4, 0.3, 0.2 or any value or range of values therebetween in 0.01% increments (e.g., about 0.35%).

In one embodiment, the $C_{max}$ (peak plasma concentration) of solanorubin in the pharmaceutical composition may range from about 0.15 ug/mL to about 0.5 ug/mL, or from about 0.12 ug/mL to about 0.55 ug/mL. In a second embodiment, the $t_{max}$ (time to reach the peak plasma concentration) of solanorubin in the pharmaceutical composition may range from about 1.5 to about 265 minutes, or from about 1 to about 290 minutes. In a third embodiment, the $t_{1/2}$ (half-life) of solanorubin in the pharmaceutical composition may range from about 1800 minutes to about 2500 minutes, or from about 1600 minutes to about 2700 minutes.

In one embodiment, the $C_{max}$ of octohydrogenosolanorubin in the pharmaceutical composition may range from about 0.05 ug/mL to about 0.3 ug/mL, or from about 0.04 ug/mL to about 0.33 ug/mL. In a second embodiment, the $t_{max}$ of octohydrogenosolanorubin in the pharmaceutical composition may range from about 1.8 minutes about 132 minutes, or from about 1.5 minutes to about 145 minutes. In a third embodiment, the $t_{1/2}$ of octohydrogenosolanorubin in the pharmaceutical composition may range from about 885 minutes to about 1900 minutes, or from about 800 minutes to about 2050 minutes.

In one embodiment, the $C_{max}$ of hexahydrogenosolanorubin in the pharmaceutical composition may range from about 0.08 ug/mL to about 0.31 ug/mL, or from about 0.07 ug/mL to about 0.34 ug/mL. In a second embodiment, the $t_{max}$ of hexahydrogenosolanorubin in the pharmaceutical composition may range from about 1.8 minutes about 265 minutes, or from about 1.5 minutes to about 288 minutes. In a third embodiment, the $t_{1/2}$ of hexahydrogenosolanorubin in the pharmaceutical composition may range from about 1250 minutes to about 1900 minutes, or from about 1110 minutes to about 2050 minutes.

The present invention also provides pharmaceutical compositions comprise (a) one or more micelles; and (b) one or more carotenoids, wherein the micelles are in an aqueous solution. In one embodiment, the carotenoids encapsulated in the micelle. In another embodiment, the encapsulation efficiency of the pharmaceutical composition is higher than 60, 70, or 80%.

In one embodiment, the micelle comprises a mixture of surfactant and phospholipid. Without being bound by any particular theory, it is believed that the weight % of the surfactant, phospholipid and oil plays an important role in the formation of the carotenoid-micelle. This is because carotenoid (such as solanorubin) is highly viscous and it is difficult to form micelle. The formation of micelle improves the bioavailability and stability of the encapsulated carotenoid. The addition, the micelle is water soluble and can be administered by IV route.

In one exemplary embodiment, about 1 to about 20 weight percent of the composition is a surfactant. In an exemplary embodiment, the weight % of the surfactant relative to the composition is equal to or less than about 19 18, 17, 16, 15, 14, 13, 12, 11, 10, 9, 8, 7 or 6, 5, 4, 3, 2 or any value or range of values therebetween in 0.1% increments (e.g., about 9.9%, about 7.4%, etc.). In another exemplary embodiment, the weight % of the surfactant relative to the composition is about 5 to about 15. In another exemplary embodiment, the weight % of the surfactant relative the composition is about 10.

In one embodiment, about 0.01 to about 2 weight percent of the composition is a phospholipid. In an exemplary embodiment, the weight % of the phospholipid of the composition is equal to or less than about 1.95, 1.9, 1.85, 1.8, 1.75, 1.7, 1.65, 1.6, 1.5, 1.45, 1.4, 1.35, 1.3, 1.25, 1.2, 1.15, 1.1, 1.05, 1, 0.95, 0.9, 0.85, 0.8, 0.75, 0.7, 0.65, 0.6, 0.5, 0.45, 0.4, 0.35, 0.3, 0.25, 0.2, 0.15, 0.1, 0.05 or any value or range of values therebetween in 0.01% increments (e.g., about 0.06%). In another exemplary embodiment, the weight % of the phospholipid relative to the composition is about 0.01% to equal to or less than about 1%. In yet another exemplary embodiment, the weight % of the phospholipid of the composition relative to the composition is about to about 0.01% to equal to or less than about 0.5. In yet another exemplary embodiment, the weight % of the phospholipid relative to the composition is about to about 0.01% to equal to or less than about 0.1.

In one embodiment, the pharmaceutical composition further comprises about 0.001 weight % to about 1 weight % beta-carotene. In another embodiment, the weight % of beta-carotene relative to the composition is equal to or less than about 0.9, 0.8, 0.7, 0.6, 0.5, 0.4, 0.3, 0.2, 0.1 or any value or range of values therebetween in 0.001% increments (e.g., about 0.001 to about 0.01%).

The diameter of the micelle maybe greater than or equal to about 1 nm, such as, for example, about 1.5 nm, about 2 nm, about 2.5 nm, about 3 nm and about 3.5 nm. The diameter of the micelle maybe less or equal to about 10 nm, such as, for example, about 9.5 nm, about 9 nm, and about 8 nm. In one embodiment, the diameter of the micelles is about 3.5 nm, about 5 nm or about 7.5 nm.

The total amount of the carotenoid in the micelle is reduced compare to the total amount of the carotenoid in the chylomicron of the present invention. In one exemplary embodiment, about 0.001 to about 1 weight % of the pharmaceutical composition is a solanorubin. In an exemplary embodiment, the weight % of solanorubin relative to the composition is equal to or less than about 0.9, 0.8, 0.7, 0.6, 0.5, 0.4, 0.3, 0.2, 0.1, or any value or range of values therebetween in 0.001% increments (e.g., 0.035%, about 0.022%, etc.). In another exemplary embodiment, the weight % of solanorubin relative to the composition is about 0.035.

In one exemplary embodiment, about 0.001 to about 1 weight percent of the composition is octohydrogenosolanorubin. In an exemplary embodiment, the weight % of octohydrogenosolanorubin relative to the composition is equal to or less than about 0.9, 0.8, 0.7, 0.6, 0.5, 0.4, 0.3, 0.2, 0.1, or any value or range of values therebetween in 0.0001% increments (e.g., 0.0027%, about 0.0053%, etc.). In another exemplary embodiment, the weight % of octohydrogenosolanorubin relative to the composition is about 0.0035.

In one exemplary embodiment, about 0.001 to about 1 weight % of the composition is a hexahydrogenosolanorubin. In an exemplary embodiment, the weight % of hexahydrogenosolanorubin of the composition is equal to or less than about 0.9, 0.8, 0.7, 0.6, 0.5, 0.4, 0.3, 0.2, 0.1, or any value or range of values therebetween in 0.0001% increments (e.g., 0.0047%, about 0.0483%, etc.). In another exemplary embodiment, the weight % of hexahydrogenosolanorubin of the composition is about 0.003.

The pharmaceutical composition may be constituted into any form suitable for the mode of administration selected. Preferably, the pharmaceutical composition comprising one or more micelles is formulated for intravenous administration. Other medically acceptable route of administration includes oral, subcutaneous, intramuscular, transdermal, rectal or inhalation and the like.

A pharmaceutical composition may be administered in a single dose treatment or in multiple dose treatments, on a schedule, or over a period of time appropriate to the disease being treated, the condition of the recipient and the route of administration. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The dosage of the pharmaceutical composition or the carotenoid can be determined by the skilled person in the art according to the embodiments. Unit doses or multiple dose forms are contemplated, each offering advantages in certain clinical settings. According to the present invention, the actual amount of carotenoid or pharmaceutical composition to be administered can vary in accordance with the age, weight, condition of the subject to be treated and other co-morbidity, and depends on the discretion of medical professionals.

The pharmaceutical composition is optionally sterilized and/or lyophilized. The pharmaceutical composition may be in the form of lyophilized powders and further diluted or reconstituted in an aqueous solution such as sterile water, saline or other suitable fluid for injection. In one embodiment, the pharmaceutical composition provided herein further comprises at least one cryoprotectant such as mannitol, glycerol, dextrose, sucrose, and/or trehalose. In some embodiments, the pharmaceutical composition further comprises at least one pharmaceutically acceptable carrier or excipient, diluent, vehicle, medium for the active ingredient, or a combination. In one embodiment, the pharmaceutical acceptable excipient is tocopherol. The weight of the carrier of excipient, per dose of a pharmaceutical composition, is about 0.001 mg to about 50 mg. In one embodiment, the weight of an acceptable carrier, per dose of a pharmaceutical composition, is about 0.01 mg to about 30 mg. In another embodiment, the weight of an acceptable carrier, per dose of a pharmaceutical composition, is about 0.1 mg to about 10 mg. In yet another embodiment, the weight % of the carrier or excipient relative to the pharmaceutical composition is about 0.001 to about 5. In an exemplary embodiment, the weight % of the carrier or excipient relative to the pharmaceutical composition is equal to or less than about 5, 4, 3, 2, 1 or any value or range of values therebetween in 0.001% increments (e.g., 1.430%, 0.012%, 000.1%-0.5%).

In one embodiment, the $C_{max}$ of solanorubin in the pharmaceutical composition may range from about 0.24 ug/mL to about 3.8 ug/mL, or from about 0.22 ug/mL to about 4.2 ug/mL. In a second embodiment, the $t_{max}$ of solanorubin in the pharmaceutical composition may range from about 1.8 to about 132 minutes, or from about 1.6 to about 145 minutes. In a third embodiment, the $t_{max}$ of solanorubin in the micellar composition may range from about 520 minutes to about 1560 minutes, or from about 460 minutes to about 2080 minutes.

In one embodiment, the $C_{max}$ of octohydrogenosolanorubin in the pharmaceutical composition may range from about 0.05 ug/mL to about 1.76 ug/mL, or from about 0.04 ug/mL to about 1.95 ug/mL. In a second embodiment, the $t_{max}$ of octohydrogenosolanorubin in the pharmaceutical composition may range from about 1.8 minutes about 66 minutes, or from about 1.5 minutes to about 75 minutes. In a third embodiment, the $t_{1/2}$ of octohydrogenosolanorubin in the pharmaceutical composition may range from about 565 minutes to about 1620 minutes, or from about 500 minutes to about 1765 minutes.

In one embodiment, the $C_{max}$ of hexahydrogenosolanorubin in the pharmaceutical composition may range from about 0.11 ug/mL to about 3 ug/mL, or from about 0.10 ug/mL to about 3.3 ug/mL. In a second embodiment, the $t_{max}$ of hexahydrogenosolanorubin in the pharmaceutical composition may range from about 1.8 minutes about 132 minutes, or from about 1.5 minutes to about 145 minutes. In a third embodiment, the $t_{1/2}$ of hexahydrogenosolanorubin in the pharmaceutical composition may range from about 565 minutes to about 2865 minutes, or from about 500 minutes to about 3130 minutes.

The following examples further illustrate the present invention. These examples are intended merely to be illustrative of the present invention and are not to be construed as being limiting

Example 1

Preparation of Pharmaceutical Composition Comprising Chylomicrons and Carotenoid One embodiment of the present invention was prepared by the following steps:
(1) A highly viscous carotenoid mixture (MCS®, commercially available from Health Ever-Biotech, Co. Ltd., Taiwan), comprises 15 mg of solanorubin (a carotenoid), 1.5 mg of octohydrogenosolanorubin (a carotenoid), 1.25 mg of hexahydrogenosolanorubin (a carotenoid), 25 mg of lecithin (phospholipid) and 1.5 mg of phytosterol, 5 mg of tocopherol, 0.5 mg of beta-carotene, was thoroughly mixed with 300.25 mg of soybean oil (a triglyceride).
(2) The mixture in step (1) was sonicated for 30 min to obtain a less viscous water/oil (W/O) emulsion (less viscous compare to the MCS® carotenoid mixture).

The pharmaceutical composition in step (2) comprises 4.3 weight % solanorubin (carotenoid), 0.43 weight % octohydrogenosolanorubin (carotenoid), 0.35 weight % hexahydrogenosolanorubin (carotenoid), 1.43 weight % tocopherol, 0.14 weight % beta-carotene, 0.43 weight % phytosterol, 7.14 weight % lecithin (phospholipid), 85.78 weight % soybean oil (triglyceride).

However, the viscous W/O emulsion in step (2) was difficult for intravenous and/or oral administration. Thus, this emulsion was optionally dissolved in 5.4 mL of deionized water containing 0.6 g of lecithin (a phospholipid) prior to feeding.

The average size of the chylomicron in aqueous solution as determined by DLS was about 131.5 nm with a polydispersity of 0.053, while the surface morphology captured by TEM revealed the encapsulation of solanorubin in chylomicron W/O emulsion with shape being roughly spherical. A high stability of solanorubin, octohydrogenosolanorubin and hexahydrogenosolanorubin was observed for chylomicron when stored at 4° C. or 25° C. for 3 months or heated at 100° C. for 4 h, as only a minor change in concentration was shown. Likewise, when chylomicron was stored at pH 2.0, 3.5, 6.0, 6.8 and 7.4 for 1, 2, 4, 6, 12 or 24 h, the stability of solanorubin, octohydrogenosolanorubin and hexahydrogenosolanorubin was maintained. The encapsulation efficiency of solanorubin in chylomicron was assessed to be approximately 80%.

Example 2

Preparation of Pharmaceutical Composition Comprising Micelles and Carotenoid

One embodiment of the present invention was prepared by the following steps:
(1) 50 mg of highly viscous carotenoid mixture, comprises (a) 2.2 mg of solanorubin (a carotenoid), (b) 0.21 mg of octohydrogenosolanorubin (a carotenoid), (c) 0.18 mg of hexahydrogenosolanorubin (a carotenoid), (d) 3.28 mg of lecithin (a phospholipid), (e) 0.71 mg of tocopherol, (f) 0.07 mg of beta-carotene and (g) 42.9 mg of oil, was thoroughly mixed with 600 mg of Tween 80 (a surfactant) in a glass tube. The mixture was stirred until it became homogeneous.

(2) The mixture in step (1) was mixed with 5.4 mL (equivalent to 5.4 g) of deionized water, and sonicated for 30 min.

(3) The mixture in step (2) was settled at room temperature for 24 h to obtain micelles (O/W emulsion), wherein the concentration of solanorubin is about 0.37 mg/mL.

The pharmaceutical composition in step (3) comprises 0.035 weight % solanorubin, 0.0035 weight % octohydrogenosolanorubin, 0.003 weight % hexahydrogenosolanorubin, 0.012 weight % tocopherol, 0.0012 weight % beta-carotene, 0.0035 weight % phytosterol, 0.06 weight % lecithin, 89.27 weight % water, 0.71 weight % oil, 9.9 weight % Tween 80.

The average size of the micelle, based on DLS and TEM analyses, was approximately 7.5 nm, with spherical shape and transparent appearance. Additionally, the particle size distribution was narrow with a low polydispersity of 0.033, indicating that a highly homogeneous microemulsion was successfully prepared. During storage at 4° C. or 25° C. for 3 months or heated at 100° C. for 4 h, only a minor difference in particle size (7.0-7.5 nm) and shape was shown for solanorubin micelle, demonstrating a high stability of this solanorubin microemulsion. Also, the mean values of solanorubin, octohydrogenosolanorubin and hexahydrogenosolanorubin were ranged from 0.34-0.38 mg/mL, 0.03-0.04 mg/mL and 0.03-0.04 mg/mL, respectively, during storage or heating under the same condition. Likewise, only a minor change in concentrations of solanorubin, octohydrogenosolanorubin and hexahydrogenosolanorubin was found when micelles were stored at pH 2.0, 3.5, 6.0, 6.8 and 7.4 for 1, 2, 4, 6, 12 or 24 h. The encapsulation efficiency of solanorubin in micelle was determined to be about 78%.

Example 3

Pharmacokinetic Study of the Pharmaceutical and Pharmaceutical Compositions

The pharmacokinetic properties of the pharmaceutical composition prepared in Example 1 and the pharmaceutical composition prepared in Example 2 were assessed in male Sprague-Dawley rats.

A total of 24 rats (all rats with body weight of about 280 g each) were divided into two groups with 12 each, one received oral administration (gavage) while the other received intravenous (i.v.) injection. In this study the solanorubin alone treatment was not included as solanorubin is practically insoluble in water, making it difficult for oral administration or i.v. injection.

The pharmaceutical composition in Example 1 and the pharmaceutical composition in Example 2 were administered via gavage and intravenous (IV) injection. An equivalent of 1.43 mg/kg of solanorubin was given by IV route (one-tenth of oral dosage) and an equivalent of 14.3 mg/kg of solanorubin was administered orally. These doses was selected based on several pre-experiments, indicating the saturation of lycopene absorption may occur at a dose higher than 14.3 mg/kg BW.

Blood samples were collected via the tail vein of the rats at the following time intervals: 2 minutes, 5 minutes, 10 minutes, 30 minutes, 1 hour, 2 hours, 4 hours, 8 hours, 24 hours, 48 hours and 72 hours after the composition was administered.

Pharmacokinetic study was carried out using the WinNonlin software system (Pharsight Co, Mountain View, Calif., USA) by non-compartmental model. The area under the drug concentration-time curve (AUC) was used to determine total amount of all-trans-solanorubin, cis-solanorubin, octohydrogenosolanorubin and hexahydrogenosolanorubin to reach the systematic circulation. Some other kinetic parameters such as $C_{max}$, $T_{max}$, and $t_{1/2}$ were measured as well. The absolute bioavailability of trans-solanorubin, cis-solanorubin, octohydrogenosolanorubin and hexahydrogenosolanorubin was calculated using the following formula:

$$\text{Absolute bioavailability}(\%) = \frac{(AUC\infty)Po/DoPo(\text{dose by gavage})}{(AUC\infty)iv/Doiv(\text{dose by } iv)} \times 100\%$$

All the data were subjected to analysis of variance and Duncan's multiple range test using Statistical Analysis Software (SAS)[16] for statistical significance at $P<0.05$.

Table 1 shows the pharmacokinetics of the pharmaceutical compositions prepared in Example 1 (chylomicron) and Example 2 (micelle).

TABLE 1

| | | | Pharmacokinetics | | | |
|---|---|---|---|---|---|---|
| Route | Composition | Ingredient | $T_{max}$ (min) | $C_{max}$ (μg/mL) | $t_{1/2}$ (min) | AUC (min μg/mL) |
| IV (1.43 mg/kg BW) | Micelle | Solanorubin | 2.0 ± 0.5 | 3.5 ± 0.8 | 577 ± 63 | 733 ± 84 |
| | | Octohydrogenosolanorubin | 2.0 ± 0.4 | 1.6 ± 0.3 | 630 ± 85 | 488 ± 67 |
| | | Hexahydrogenosolanorubin | 2.0 ± 0.3 | 2.7 ± 0.6 | 630 ± 78 | 651 ± 74 |
| | Chylomicron | Solanorubin | 2.0 ± 0.03 | 0.45 ± 0.06 | 2310 ± 246 | 530 ± 49 |
| | | Octohydrogenosolanorubin | 2.0 ± 0.6 | 0.27 ± 0.05 | 1732 ± 198 | 177 ± 58 |
| | | Hexahydrogenosolanorubin | 2.0 ± 0.4 | 0.28 ± 0.03 | 1732 ± 216 | 107 ± 36 |
| Oral (14.3 mg/kg BW) | Micelle | Solanorubin | 120 ± 19 | 0.27 ± 0.03 | 1732 ± 198 | 496 ± 57 |
| | | Octohydrogenosolanorubin | 60 ± 12 | 0.06 ± 0.01 | 1470 ± 126 | 209 ± 24 |
| | | Hexahydrogenosolanorubin | 120 ± 18 | 0.13 ± 0.02 | 2605 ± 354 | 204 ± 28 |

TABLE 1-continued

| Route | Composition | Ingredient | Pharmacokinetics | | | |
|---|---|---|---|---|---|---|
| | | | $T_{max}$ (min) | $C_{max}$ (µg/mL) | $t_{1/2}$ (min) | AUC (min µg/mL) |
| | Chylomicron | Solanorubin | 240 ± 30 | 0.18 ± 0.04 | 2018 ± 326 | 503 ± 68 |
| | | Octohydrogen-osolanorubin | 120 ± 18 | 0.06 ± 0.03 | 985 ± 143 | 166 ± 23 |
| | | Hexahydrogen-osolanorubin | 240 ± 26 | 0.09 ± 0.05 | 1386 ± 196 | 76 ± 15 |

The bioavailability of the orally administered pharmaceutical compositions are shown in Table 2.

TABLE 2

| Route | Composition | Ingredient | Bioavailability % |
|---|---|---|---|
| Oral (14.3 mg/kg BW) | Micelle | Solanorubin | 6.8 |
| | | Octohydrogenosolanorubin | 4.3 |
| | | Hexahydrogenosolanorubin | 3.1 |
| | Chylomicron | Solanorubin | 9.5 |
| | | Octohydrogenosolanorubin | 9.4 |
| | | Hexahydrogenosolanorubin | 7.1 |

Referring to Table 1, the maximum plasma concentration ($C_{max}$, µg/mL) of solanorubin, octohydrogenosolanorubin and hexahydrogenosolanorubin was 0.27, 0.06 and 0.13 µg/mL at 120, 60 and 120 min post oral administration of the micelle composition. The $C_{max}$ (µg/mL) of solanorubin, octohydrogenosolanorubin and hexahydrogenosolanorubin was 0.18, 0.06 and 0.09 at 240, 120 and 240 min post oral administration of the chylomicron composition. It took a shorter time for the micelle composition to achieve $C_{max}$ compare to the chylomicron composition, due to micelle's smaller particle size.

The AUC (min µg/mL) for solanorubin, octohydrogenosolanorubin and hexahydrogenosolanorubin were 496, 209 and 204 for the orally administered micelle composition, and were 503, 166 and 76 for the orally administered chylomicron composition.

The $C_{max}$ for solanorubin, octohydrogenosolanorubin and hexahydrogenosolanorubin were 3.5, 1.6 and 2.7 µg/mL at 2, 2 and 2 min post IV administration of the micelle composition. The $C_{max}$ for solanorubin, octohydrogenosolanorubin and hexahydrogenosolanorubin were 0.45, 0.27 and 0.28 µg/mL at 2, 5 and 2 min respectively after IV administration of chylomicron composition. The $C_{max}$ of solanorubin, octohydrogenosolanorubin and hexahydrogenosolanorubin for the IV administered micelle composition was 7.8-, 5.9- and 9.6-fold higher than those of IV administered chylomicron composition due to the smaller mean particle size of the micelle.

Similarly, The AUC (min µg/mL) for solanorubin, octohydrogenosolanorubin and hexahydrogenosolanorubin were higher for the IV administered micelle composition, (by 203, 311 and 544, respectively) compare to those of IV administered chylomicron composition.

Table 2 shows the oral bioavailability of solanorubin (include all-trans and cis-isomers of solanorubin), octohydrogenosolanorubin and hexahydrogenosolanorubin for the orally administered micelle composition were 6.8, 4.3 and 3.1%, respectively, whereas the bioavailability of solanorubin (include all-trans and cis-isomers of solanorubin), octohydrogenosolanorubin and hexahydrogenosolanorubin for the orally administered chylomicron composition was 9.5, 9.4 and 7.1% respectively. Compared to the micelle composition, the chylomicron composition provided a higher bioavailability of the carotenoids. Without being bind by any particular theory, it is believed that the chylomicron provided a better protection for the carotenoids during digestion and absorption, as evidenced by a thicker outer layer of chylomicron. The bioavailability of solanorubin in the micelle and chylomicron were both higher than that of non-encapsulated solanorubin. (1.85%, see Faisal et al "Bioavailability of solanorubin in the rat: the role of lymphatic transport. J. Pharm. Pharmacol. 2010, March 62(3):323-31).

The disclosures of each patent, patent application, and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A pharmaceutical composition, comprising:
   (a) a chylomicron comprising a mixture of triglyceride, phospholipid and phytosterol, wherein the ratio of triglyceride:phospholipid:phytosterol relative to the pharmaceutical composition ranges from about 80:5:0.1 (w/w) to about 92:12:1 (w/w); and
   (b) a carotenoid.

2. The pharmaceutical composition of claim 1, wherein the ratio of phytosterol is about 0.7 (w/w).

3. The pharmaceutical composition of claim 1, further comprising a pharmaceutically acceptable carrier or excipient.

4. The pharmaceutical composition of claim 3, wherein the pharmaceutically acceptable excipient is tocopherol.

5. The pharmaceutical composition of claim 1, wherein the triglyceride is selected from soy bean oil, pumpkin seed oil, linseed oil, grapeseed oil, olive oil, sunflower seed oil and combination thereof.

6. The pharmaceutical composition of claim 1, wherein the phospholipid is selected from lecithin and phosphatidylcholine.

7. The pharmaceutical composition of claim 1, wherein the carotenoid is carotene.

8. The pharmaceutical composition of claim 1, wherein the carotenoid is selected from solanorubin; octohydrogenosolanorubin, hexahydrogenosolanorubin and combination thereof.

9. The pharmaceutical composition of claim 8, wherein the weight ratio of solanorubin, octohydrogenosolanorubin and hexahydrogenosolanorubin relative to the pharmaceutical composition is about 4-5:0.1-1:0.1-1.

10. The pharmaceutical composition of claim 9, wherein the weight ratio of solanorubin:octohydrogenosolanorubin:

hexahydrogenosolanorubin is about 4.2-4.5:0.3-0.5:0.3-0.5 relative to the pharmaceutical composition.

11. The pharmaceutical composition of claim 1, wherein the diameter of the chylomicron is about 75 to about 450 nm.

12. The pharmaceutical composition of claim 1, wherein the diameter of the chylomicron is about 100 to about 150 nm.

13. The pharmaceutical composition of claim 1, wherein the carotenoid is encapsulated in the chylomicron.

14. The pharmaceutical composition of claim 1, wherein the AUC of solanorubin is about 450 to 580 min μg/mL.

15. The pharmaceutical composition of claim 1, wherein the AUC of octohydrogenoso-lanorubin is about 150 to about 200 min μg/mL.

16. The pharmaceutical composition of claim 1, wherein the AUC of hexahydrogenoso-lanorubin is about 65 to about 120 min μg/mL.

17. The pharmaceutical composition of claim 1, further comprising a beta-carotene.

18. The pharmaceutical composition of claim 1, wherein the pharmaceutical composition is constituted with water and phospholipid prior to use.

* * * * *